United States Patent [19]

Trimmer et al.

[11] 4,431,006
[45] Feb. 14, 1984

[54] PASSIVE ULTRASOUND NEEDLE PROBE LOCATOR

[75] Inventors: William S. Trimmer, Belle Mead; Bayard Gardineer, Jr., Skillman; Andreas Hadjicostis, North Brunswick, all of N.J.

[73] Assignee: Technicare Corporation, Solon, Ohio

[21] Appl. No.: 337,899

[22] Filed: Jan. 7, 1982

[51] Int. Cl.³ .............................................. A61B 10/00
[52] U.S. Cl. .................................. 128/660; 128/24 A
[58] Field of Search ............................... 128/660–663, 128/24 A

[56] References Cited

U.S. PATENT DOCUMENTS

| | | |
|---|---|---|
| 3,556,079 | 1/1971 | Omizo . |
| 3,721,227 | 3/1973 | Larson et al. . |
| 3,896,811 | 7/1975 | Storz ............................ 128/24 A X |
| 4,029,084 | 6/1977 | Soldner . |
| 4,058,114 | 11/1977 | Soldner . |
| 4,108,165 | 8/1978 | Kopp et al. . |
| 4,249,539 | 2/1981 | Vilkomerson ...................... 128/660 |
| 4,330,278 | 5/1982 | Martin ........................... 128/24 A X |

FOREIGN PATENT DOCUMENTS 2455401 11/1974 Fed. Rep. of Germany .

OTHER PUBLICATIONS

Time, Oct. 2, 1964, p. 96, "Surgery, Into the Eye with Ultrasound."

*Primary Examiner*—Kyle L. Howell
*Assistant Examiner*—Francis J. Jaworski

[57] ABSTRACT

A solid steel stylet is carried coaxially within a hollow biopsy needle. The stylet carries a matching layer at its tip, such that when the needle and stylet are inserted into the body, ultrasound energy impinging on the needle tip is converted to pressure waves which are conveyed back up the stylet. An ultrasound transducer located outside the body is coupled to receive sonic energy from the stylet, and to convert it to electrical energy for coordination with, and superposition upon the image of the system.

16 Claims, 10 Drawing Figures

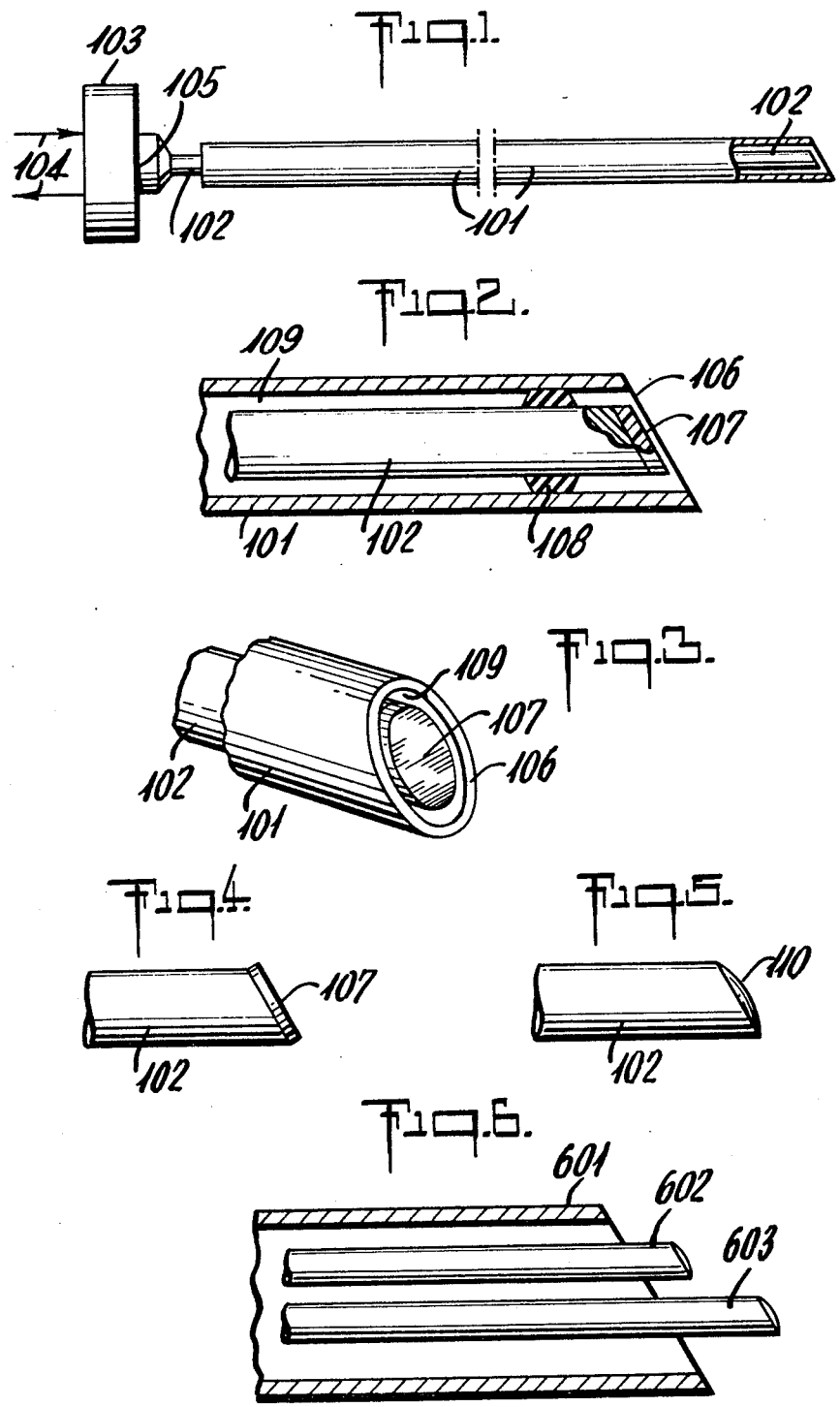

PASSIVE ULTRASOUND NEEDLE PROBE LOCATOR

FIELD OF THE INVENTION

This invention relates to ultrasound imaging systems, and more particularly to methods and apparatus for the utilization of such systems to track and control the location of needle probes within the body.

BACKGROUND OF THE INVENTION

Ultrasound imaging systems are finding increased popularity for use in conjunction with needle probes inserted into the body, for example for purposes of aspiration biopsy. Traditionally, it was held that the very high sonic impedance of the needles (traditionally stainless steel) made it difficult if not impossible to locate the needle precisely through the conventional pulse echo methods of ultrasound imaging systems. That is, sonic wavefronts passing through soft tissue, when they impinged upon the needle, would be scattered unpredictably and hence could not be precisely located in the field of the image. Hence, numerous prior art patents feature a needle entry either through the center of, or at least coaxial with the application of sonic energy into the patient. Only when the needle digresses from the normal would any signals show up in the system, and hence those prior art systems rely on absence of needle signal, rather than presence of needle signal, to indicate proper direction. Clearly, however, those systems do not give an adequate indication of needle depth, and are extremely inconvenient to use due to their necessity of applying the needle at the point of the transducer.

U.S. Pat. No. 4,249,539 to Vilkomerson et al., issued Feb. 10, 1981, and entitled "Ultrasound Needle Tip Localization System", addresses the problems attendant to the above-described prior art systems, and posits a solution based on location of a miniature transducer at the tip of the penetrating needle. This transducer, which functions essentially as a point source transducer and acts in addition to the external, ultrasound imaging system transducer, constitutes an active sonic receiver at the needle point, which is coupled to associated processing apparatus through electrical conduits within the needle, and hence is enabled to generate return signals from the needle point to the system transducer. Alternatively, it forms the basis for superposition of the needle point on the system image, based on the time of flight between the generation of an imaging pulse at the system transducer, and the receipt thereof at the point transmitter associated with the needle. In accordance with the teachings of the Vilkomerson et al. patent, once the needle is properly positioned, the point source transducer may be withdrawn from the needle, and aspiration biopsy, insertion of drugs or markers, or the like may be conducted through the needle in conventional fashion.

The systems and methods set forth in the Vilkomerson et al. patent do provide a viable, accurate approach to the localization of the needle probe. Such approach is not without its problems, however. First, a point source transducer for maintenance at the needle tip, and withdrawal through the needle, is not inexpensive, and in any event requires placement of an active electrical element deep within the body of the patient. Secondly, necessity to have the transducer penetrate human flesh requires sterilization, another inconvenient and expensive requirement. Finally, some forms of transducer adequate in size and configuration for applications in accordance with the Vilkomerson patent, for example those configured of polyvinylidine fluoride (PVF2), provide relatively low electrical signal levels, and hence necessitate relatively complex and expensive signal processing systems outside the body.

It is accordingly an object of the present invention to provide systems of the sort set forth in the Vilkomerson et al. patent, but which obviate the need for locating active electrical elements within the patient's body, and hence likewise obviate safety difficulties attendant thereto, and difficulties attendant to sterilization of such active elements.

SUMMARY OF THE INVENTION

The principles of the present invention are premised upon utilization of a stylet-like passive element for sensing sonic pulses in the body and conveying those pulses, as sonic energy, out through the needle, where they are converted to electrical energy. Thus, a coaxial needle probe carries a coaxial conduit rod during insertion, which terminates in the region of the needle tip, as desired either just outside, at, or within the needle tip. The stylet conduit is coupled to a transducer outside the body, such that ultrasound pressure waves which are conducted through the needle and out of the body are only then converted to electrical energy. Hence, the only portion of the apparatus which penetrates and/or contacts body tissues are the electrically passive, essentially disposable and easily sterilizable needle and stylet portions.

In a preferred embodiment, the stylet—sonic conduit is fashioned of stainless steel, and terminates in a sonic matching layer. The stylet—conduit is isolated from the interior surface of the needle either by spacing or by insulating materials.

DESCRIPTION OF THE DRAWINGS

FIG. 1 shows an illustrative embodiment of the principles of the present invention, including needle, stylet, and outside the body transducer means;

FIG. 2 shows a partial cutaway, magnified and distorted for convenience of explanation, with respect to the embodiment of FIG. 1;

FIG. 3 shows an isometric illustration of the point region of the embodiment of FIG. 1;

FIGS. 4 and 5 show alternative embodiments of stylet conduits in accordance with the principles of the present invention; and FIGS. 6, 7A, 7B, 8A and 8B show alternative embodiments of the principles of the present invention.

BEST MODE FOR CARRYING OUT THE INVENTION

Figure 7A:
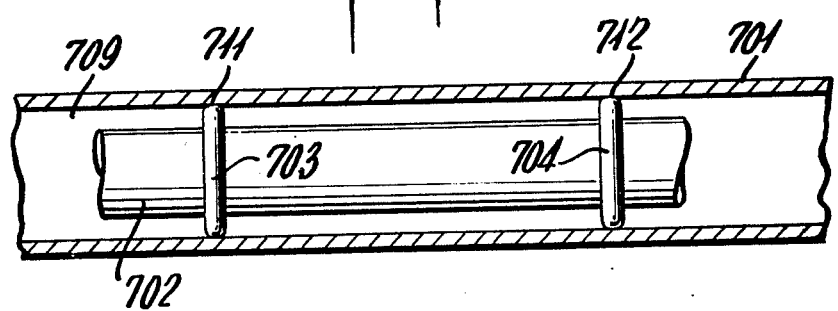

As summarized hereinbefore, the principles of the present invention relate essentially to the apparatus and methods for picking up sonic pulses in the body, and conveying them, in the form of sonic pulses, through the needle, out of the body, and to an external transducer which converts the sonic pulses to electrical energy. Thereupon, the electrical representations of the sonic pulses so sensed, are utilized in ultrasound imaging systems in order to display the composite needle probe and tissue image. Particular attention is therefore drawn to the aforementioned U.S. Pat. No. 4,249,539 to Vilkomerson et al., which for purposes of completing the instant disclosure, is hereby incorporated by reference herein. In brief, the essence of the Vilkomerson et al. patent is the location of a point source transducer at the needle tip, the withdrawal of electrical signals from the transducer through the needle, and the utilization of those electrical signals in a system which is disclosed in some detail therein. In accordance with the principles of the present invention, it is foreseen that substantially the same systems and circuitry would be utilized, with the preferred system being that set forth in FIGS. 3 and 4 of the Vilkomerson et al. patent, that is apparatus wherein the needle tip image is merged with the tissue image by superposition of the signal which is sensed by and withdrawn through the needle. In the Vilkomerson et al. patent, electrical signals are generated at the needle tip, and hence are substantially instantaneously received at the circuitry for processing the signals. In accordance with the principles of the present invention, pressure waves in the form of sonic energy are conveyed up through the needle, hence requiring some small further delay (e.g. 10 microseconds) in the processing of the composite image, simply to account for the time of flight of its sonic pulse out through the needle via the ultrasound conduit carried therein. Such an adjustment to the system of Vilkomerson et al. may be simply achieved either by inserting a small delay in the imaging control 303, or alternatively adjusting the counts of the time delay logic 305, which is shown in considerable detail in FIG. 4. In any event, such minor adjustment is, in view of the disclosure of the Vilkomerson et al. patent, well within the capability of those of ordinary skill in the art.

Referring, then, to the instant figures, there are shown various illustrative and preferred embodiments of the principles of the present invention. In FIG. 1, a hollow needle 101, shown foreshortened for convenience, carries therein a stylet 102 which extends from the proximate end of the needle (i.e. the end which stays outside the body) through the needle to the distal end thereof (i.e. the end which penetrates the body). In FIG. 1, the distal end of the needle 101 is cut away, revealing the stylet 102 which extends approximately to the distal opening of the needle 101. At the proximate end of the needle 101, the stylet 102 flares outwardly and, at a surface 105 abuts a transducer 103. As is conventional in the art, impinging sonic pulses at surface 105 excite a piezoelectric response in the transducer 103, and electrical signals are generated, as indicated symbolically by connections 104. It has been found that physically abutting complementary surfaces at 105 are adequate in accordance with the principles of the present invention, but that the conduct of sonic energy from the stylet conduit 102 to the transducer 103 may be facilitated by utilization of gel, oil, or the like coupling media standard in the art, intermediate the stylet 102 and the transducer 103. In other forms of the present invention, the stylet 102, rather than flaring outwardly as shown in FIG. 1, tapers and is forced directly into the surface of the transducer 103. Numerous other configurations are deemed well within the purview of the principles of the present invention, provided simply that they allow the sonic energy from the stylet 102 to be coupled to the transducer 103 for adequate piezoelectric response thereat. Additionally, the transducer 103 may be the self same transducer which is utilized for the basic imaging system.

Referring next to FIG. 2, there is shown an enlarged view of the cutaway distal portion of the apparatus of FIG. 1. In FIG. 2, the needle 101 is cut away, but the stylet 102 is not. The stylet conduit 102 is generally coaxial with the needle 101, with an annular space 109 being formed to isolate the stylet 102 physically from the needle 101. It will be noted that alternative embodiments of the present invention will feature various spacers between the inner surface of the needle 101 and the stylet 102, in order to maintain spatial isolation therebetween. It is to be noted, however, that the principles of the present invention are generally operative even in the absence of any spacer between the stylet 102 and the inner surface of the needle 101, and that as the needle is inserted into the body, some small amount of bending will occur, and some minimal amount of contact will occur between the stylet 102 and the surface of the needle 101, but that such contact will not obviate the effectiveness of the principles of the present invention. In fact, some such contact may even be beneficial, tending to damp radial or transverse vibration in the stylet, and hence promote longitudinal propagation of the sensed ultrasound pressure waves. In FIG. 2, the stylet 102 is shown terminating in a matching layer 107, which is an optional but highly desirable feature in order to enhance the efficiency of translating the sonic pulses in the body into sonic pressure waves passing through the stylet conduit 102. The embodiment of FIG. 2 also shows an annulus of flexible material, for example of commercially available silicone caulking materials, which not only provides spacing between the stylet 102 and the needle 101, but more importantly serves as a gasket to prevent backflow of fluids into the needle. For ease of understanding, FIG. 3 shows a schematic isometric view of the distal point of the needle 101 and the stylet—conduit 102, in a form which has not been cut away.

It will be noted that the needle 101 itself, supplemented by the annular space 109, forms a protective sheath for the stylet 102, partially reflecting incident energy, and absorbing and substantially dissipating the balance thereof. Hence, the elongated stylet 102 within the needle 101 acquires sonic energy essentially only at the tip 107 thereof.

It will be noted from the embodiments of FIGS. 1 through 3 that the needle 106 and the stylet 102 are beveled at their terminus, at an angle of approximately 45°. Such is a rather conventional configuration, which is convenient for application in accordance with the principles of the present invention. The angle of beveling is not critical, however, inasmuch as the stylet—conduit 102 need not repose within the point of the needle 101, as is shown in the drawing. Indeed, the stylet 102 may be further extended beyond the needle point, and even rotated about in order to facilitate the sensing of sonic pulses. In a preferred embodiment, the needle 101 and the stylet—conduit 102 are both fashioned of stainless steel, while the matching layer 107 is fashioned of one of the numerous plastic or glass materials in conventional use for matching in the construction of active ultrasound transducers. For example, one such plastic is the one sold commercially under the trade designation "MF114" from Emerson-Cuming Co. In embodiments which rely on an air gap 109, such a gap of 0.001 inches will generally be adequate; in embodiments which utilize some substance in the area 109, distances equivalent to a fraction of a sonic wavelength, for example 0.01 inches, may be utilized. In preferred embodiments, the matching layer 107 will be a quarter wavelength in thickness and may in fact be constituted of a composite or sandwich layering of several matching materials. As is shown in FIGS. 2 and 4, the matching layer 107 may be disc-shaped; alternatively it may be a rounded dome shape as shown by element 110 in FIG. 5.

Referring to FIG. 6, there is shown an alternative embodiment wherein a larger bore needle 601, which can accommodate plural stylet—conduits 602, 603, and the like. In such a system, the plural stylet—conduits 602 and 603 will, in the body, have their distal ends spatially offset from one another, and hence will be impinged by each given sonic wavefront at different times. It is thereby possible, based on the time delay therebeween, to determine sonic rate of propagation, direction of propagation, doppler factors, and the like.

In use, the principles of the present invention may be applied with advantage to either the receive-superposition or the receive-transmit modes of operation as taught by Vilkomerson et al. That is, received signals may be processed outside the body and combined by superposition with the image field, or the transducer 103 may be utilized to generate a pulse which is carried down through the stylet 102 and thence out into body tissues. In the latter event, it may be desirable to produce such a return pulse after receipt of an imaging pulse. Alternatively, it may be more beneficial from the standpoint of overall system utilization to fire the stylet transducer 103 simultaneously with the firing of the imaging system transducer. Since the imaging pulse-echo process will entail a round trip propagation delay (e.g. 300 microseconds), generating a pulse at the same time from the stylet will insure that the needle point locator signal will be "heard" by the imaging system after only half the time (e.g. 150 microseconds), hence at a time when the imaging system electronics are otherwise quiescent and not otherwise gainfully employed. The system processor then will, simply through suitable delay of processing, produce the composite image including the pulse-echo signal with the point locator signal.

Figure 7B:
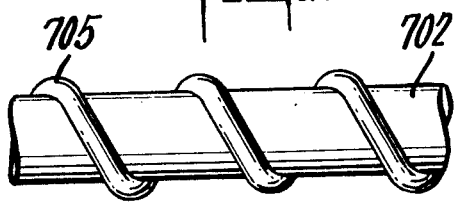
Figure 8A:
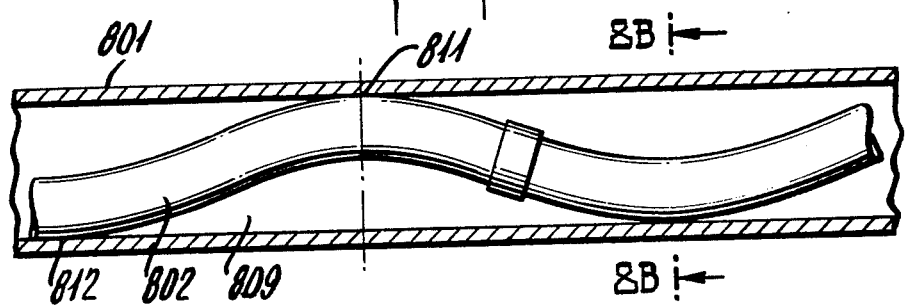
Figure 8B:
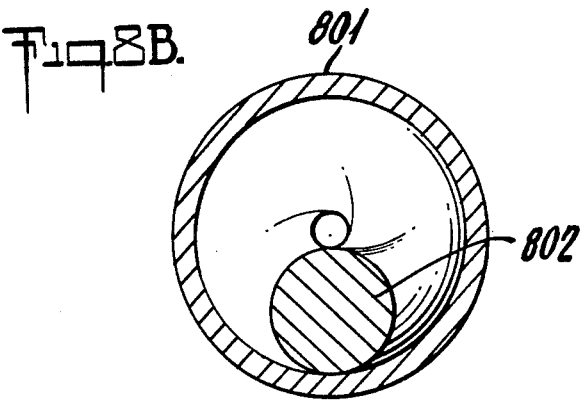

Referring next to FIGS. 7A, 7B, 8A and 8B, there are shown alternative embodiments which are intended to facilitate effective wave propagation up and down the stylet. In brief, it may be desirable to provide spacer mechanisms periodically along the length of the stylet, so that the wavefront will not dissipate along the stylet due to spurious, irregular translation of the stylet. In FIG. 7A, periodic ridges 703, 704 etc. act as spacers to insure reasonable maintenance of the gap 709 between the needle 701 and the stylet 702. In practice, the ridges 703, 704 etc. may be integral annular extensions from the stylet 702, or may be a continuous helical ridge 705 as shown in FIG. 7B. Likewise, the annuli 703 and 704, or the helix 705 may be separately affixed over the stylet 702. FIG. 8A and FIG. 8B which is a transverse section thereof, shows an alternative configuration wherein the stylet 802 is itself configured as an extended helix, periodically contacting the needle 801 and thereby being physically secure therein.

In the embodiments of FIGS. 7A and 7B, and that of FIGS. 8A and 8B, the periodic, nearly point contacts 711, 712, 811, 812, etc., provide an "anti-jiggle" security for the stylets 702, 802, respectively, but do not appreciably affect the longitudinal propagation of energy along the stylets.

It will be appreciated that the foregoing has set forth various illustrative and preferred embodiments of the principles of the present invention, but that numerous alternatives will occur to those of ordinary skill in the art without departure from the spirit or the scope of the present invention.

We claim:

1. In a system for deriving an image of a region of a body by applying ultrasound energy to the region by means of an external transducer a probe and probe locator apparatus comprising:
   (a) hollow needle means thereby defining a probe for insertion into the body; and
   (b) ultrasonic energy transmission means, a portion of which is removably located within said hollow needle means, including
      (i) passive solid conduit means, removably carried within said needle means, for detecting ultrasound energy near the tip region of said needle means and for conveying said energy through said needle means and outside the body; and
      (ii) electrically active ultrasound transducer means coupled to receive ultrasonic energy from said conduit means outside the body and adapted to produce an output signal to said system indicative thereof, whereby the location of the probe within the image area may be determined.

2. Apparatus as described in claim 1 wherein said conduit means comprises a solid, sonically conductive rod extending inside said needle means and terminating in an oblique surface cross-section.

3. Apparatus as described in claim 2 wherein said conduit means includes a matching layer, attached to said cross-section, for coupling incident sonic energy to said rod.

4. Apparatus as described in claim 2 wherein said rod is sized in cross-section to form a high sonic impedance gap to the inner surface of said needle means.

5. Apparatus as described in claim 4 wherein said gap is formed of air, and wherein said conduit means forms an annular liquid tight seal near the inserted extremity of said needle means.

6. Apparatus as described in claim 2 wherein said rod consists essentially of stainless steel.

7. Apparatus as described in claim 2 wherein said rod makes periodic, relatively short contacts with the inner surface of said needle means.

8. Apparatus as described in claim 7 wherein said rod defines periodic annular ridges spanning a gap between said rod and said needle means.

9. Apparatus as described in claim 7 wherein said rod defines a helical ridge spanning a gap between said rod and said needle means.

10. Apparatus as described in claim 1 wherein said conduit means and said transducer means are coupled to one another by simple mechanical contact.

11. Apparatus as described in claim 1 wherein said conduit means are coupled to one another through a fluid sonic coupling medium.

12. In a system for deriving an image of a region of a body by applying ultrasound energy to the region by means of an external transducer probe locator apparatus comprising:
   (a) hollow needle means for insertion into the body;
   (b) conduit means, carried within said needle means, for detecting ultrasound energy near the tip region of said needle means and for conveying said energy through said needle means and outside the body; and
   (c) ultrasound transducer means coupled to receive energy from said conduit means outside the body, wherein said conduit means comprises a solid, sonically conductive rod extending inside said needle means and terminating in an oblique surface cross-section, and wherein said conduit means comprises plural solid rods carried within said needle means and extending respective plural different distances into the body, thereby providing means for sensing the timed receipt of sonic pulses at said distances, and hence the direction and propagation speed of sonic energy in the body.

13. In a system for deriving any image of a region of a body by applying ultrasound energy to the region by means of an external transducer probe locator apparatus comprising:

(a) hollow needle means for insertion into the body;

(b) conduit means, carried within said needle means, for detecting ultrasound energy near the tip region of said needle means and for conveying said energy through said needle means and outside the body; and (c) ultrasound transducer means coupled to receive energy from said conduit means outside the body, wherein said conduit means comprises a solid, sonically conductive rod extending inside said needle means and terminating in an oblique surface cross-section, wherein said rod makes periodic, relatively short contacts with the inner surface of said needle means, and wherein said rod is helical in configuration, thereby making periodic contact with the inner surface of said needle means.

14. A method of monitoring and controlling insertion of a needle probe into the body of a subject comprising the steps of:

(a) irradiating a body area utilizing pulse echo ultrasound techniques employing a first external transducer means;

(b) providing a passive conduit means within a needle probe, said conduit means terminating in the distal tip region of the needle probe;

(c) inserting the distal tip of said needle into said body area at an angle and in a direction which are independent of the position and orientation of said transducer means;

(d) coupling sonic energy from said conduit means to a transducer means which may but need not be distinct from said first transducer means; and (e) producing a composite image of said body area, based on pulse signals incident to the distal tip of said conduit means, and upon ultrasound echo signals received by said external transducer means.

15. A method as described in claim 14 and further comprising the steps of generating a sonic pulse outside said body, sending said generated pulse down said conduit means through said needle probe, and conditioning said external transducer means to detect dispersed sonic energy from said conduit means distal tip into the body of the subject.

16. A method as described in claim 15 wherein said sonic pulse is coupled to said conduit means outside said body at approximately the same time an imaging pulse is generated at said external transducer means.

* * * * *